(12) United States Patent
Black et al.

(10) Patent No.: US 9,005,205 B2
(45) Date of Patent: Apr. 14, 2015

(54) ROD INSERTION TOOLS, RODS AND METHODS

(71) Applicant: DeGen Medical, Inc., Florence, SC (US)

(72) Inventors: Craig Black, Florence, SC (US); Willie S. Edwards, Florence, SC (US); Rakesh P. Chokshi, Florence, SC (US); John E. Pendleton, Atlanta, GA (US); Ryan A. Lewis, Waxhaw, NC (US)

(73) Assignee: DeGen Medical, Inc., Florence, SC (US)

( * ) Notice: Subject to any disclaimer, the term of this patent is extended or adjusted under 35 U.S.C. 154(b) by 29 days.

(21) Appl. No.: 13/783,728

(22) Filed: Mar. 4, 2013

(65) Prior Publication Data

US 2014/0249592 A1    Sep. 4, 2014

(51) Int. Cl.
    *A61B 17/70*    (2006.01)
(52) U.S. Cl.
    CPC ......... *A61B 17/7089* (2013.01); *A61B 17/7004* (2013.01)
(58) Field of Classification Search
    CPC ........... A61B 17/7001; A61B 17/7074; A61B 17/7085; A61B 17/7004; A61B 17/7089
    USPC ................... 606/86 A, 99, 246, 264
    See application file for complete search history.

(56) References Cited

U.S. PATENT DOCUMENTS

| | | | |
|---|---|---|---|
| 4,877,020 A * | 10/1989 | Vich | ........................... 606/86 R |
| 4,887,596 A | 12/1989 | Sherman | |
| 5,817,094 A | 10/1998 | Errico et al. | |
| 6,280,442 B1 | 8/2001 | Barker et al. | |
| 6,530,929 B1 | 3/2003 | Justis et al. | |
| 6,540,748 B2 | 4/2003 | Lombardo | |
| 7,008,422 B2 | 3/2006 | Foley et al. | |
| 7,497,869 B2 | 3/2009 | Justis | |
| 7,520,879 B2 * | 4/2009 | Justis et al. | ................. 606/86 A |
| 7,572,279 B2 | 8/2009 | Jackson | |
| 7,686,809 B2 * | 3/2010 | Triplett et al. | .............. 606/86 A |
| 7,717,944 B2 | 5/2010 | Foley et al. | |
| 7,727,261 B2 | 6/2010 | Barker et al. | |
| 7,749,232 B2 | 7/2010 | Salerni | |

(Continued)

FOREIGN PATENT DOCUMENTS

WO        WO0122893        4/2001

OTHER PUBLICATIONS

File history of U.S. Appl. No. 11/749,615, now U.S. Patent No. 7,942,910, as of Nov. 27, 2013. Filing date, May 16, 2007. First Named Inventor, Robert L. Doubler. Title, Polyaxial Bone Screw.

(Continued)

*Primary Examiner* — Pedro Philogene
*Assistant Examiner* — David Comstock
(74) *Attorney, Agent, or Firm* — Buchanan Nipper

(57) ABSTRACT

Rod insertion tools, rods and methods for placing rods in patients are described. An exemplary spinal rod insertion tool comprises a handle, a main body connected to the handle, a rod engaging member disposed within an inner passageway defined by the main body and adapted to move from an extended position to a chambered position in which the rod engaging member distal end is disposed within the inner passageway, and an adjustment mechanism operably connected to the rod engaging member and adapted to cause movement of the rod engaging member from the extended position to the chambered position.

19 Claims, 12 Drawing Sheets

(56) References Cited

U.S. PATENT DOCUMENTS

| | | |
|---|---|---|
| 7,763,055 B2 | 7/2010 | Foley |
| 7,857,834 B2 | 12/2010 | Boschert |
| 7,862,595 B2 | 1/2011 | Foley et al. |
| 7,867,259 B2 | 1/2011 | Foley et al. |
| 7,887,539 B2 | 2/2011 | Dunbar, Jr. et al. |
| 7,892,238 B2 | 2/2011 | DiPoto et al. |
| 7,918,878 B2 | 4/2011 | Songer et al. |
| 7,922,727 B2 | 4/2011 | Songer et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,173 B2 | 5/2011 | Hammill, Sr. et al. |
| 8,002,806 B2 | 8/2011 | Justis |
| 8,038,699 B2 | 10/2011 | Cohen et al. |
| 8,075,603 B2 | 12/2011 | Hammill, Sr. et al. |
| 8,092,460 B2 | 1/2012 | Geist et al. |
| 8,105,362 B2 | 1/2012 | Duarte |
| 8,123,751 B2 | 2/2012 | Shluzas |
| 8,147,522 B2 | 4/2012 | Warnick |
| 8,192,439 B2 | 6/2012 | Songer et al. |
| 8,197,518 B2 | 6/2012 | Hammill, Sr. et al. |
| 8,236,035 B1 | 8/2012 | Bedor |
| 8,246,624 B2 | 8/2012 | Forton et al. |
| 8,361,124 B2 | 1/2013 | Sherman et al. |
| RE44,813 E * | 3/2014 | Beale et al. ........... 606/86 A |
| 2002/0161368 A1 | 10/2002 | Foley et al. |
| 2003/0060826 A1 | 3/2003 | Foley et al. |
| 2005/0021031 A1 | 1/2005 | Foley et al. |
| 2006/0111714 A1 | 5/2006 | Foley |
| 2008/0004625 A1 | 1/2008 | Runco et al. |
| 2008/0125788 A1 | 5/2008 | Cohen et al. |
| 2008/0269809 A1 | 10/2008 | Garamszegi |
| 2009/0082775 A1 | 3/2009 | Altarac et al. |
| 2009/0171391 A1 | 7/2009 | Hutton et al. |
| 2009/0171392 A1 | 7/2009 | Garcia-Bengochea et al. |
| 2009/0326582 A1 | 12/2009 | Songer et al. |
| 2009/0326586 A1 | 12/2009 | Duarte |
| 2010/0145389 A1 | 6/2010 | Triplett et al. |
| 2010/0312279 A1 | 12/2010 | Gephart et al. |
| 2011/0022088 A1 | 1/2011 | Forton et al. |
| 2011/0040328 A1 | 2/2011 | Miller et al. |
| 2011/0071571 A1 | 3/2011 | Abdelgany |
| 2011/0093014 A1 | 4/2011 | Davis et al. |
| 2011/0152942 A1 | 6/2011 | Oh et al. |
| 2011/0270325 A1 | 11/2011 | Keyer et al. |
| 2012/0022597 A1 | 1/2012 | Gephart et al. |
| 2012/0041490 A1 | 2/2012 | Jacob et al. |
| 2012/0046700 A1 | 2/2012 | Jackson et al. |
| 2012/0265212 A1 | 10/2012 | Seek |
| 2012/0296380 A1 | 11/2012 | Simonson |

OTHER PUBLICATIONS

File history of U.S. Appl. No. 12/355,145, now U.S. Patent No. 7,947,065, as of Nov. 27, 2013. Filing date, Jan. 16, 2009. First Named Inventor, John E. Hammill. Title, Locking Polyaxial Ball and Socket Fastener.

File history of U.S. Appl. No. 12/700,436, now U.S. Patent No. 7,951,173, as of Nov. 27, 2013. Filing date, Feb. 4, 2010. First Named Inventor, John E. Hammill. Title, Pedicle Screw Implant System.

File history of U.S. Appl. No. 12/833,751, now U.S. Patent No. 8,075,603, as of Nov. 27, 2013. Filing date, Jul. 9, 2010. First Named Inventor, John E. Hammill. Title, Locking Polyaxial Ball and Socket Fastener.

File history of U.S. Appl. No. 13/317,969, as of Nov. 27, 2013. Filing date, Nov. 1, 2011. First Named Inventor, Roger P. Jackson. Title, Polyaxial Bone Anchor With Pop-on Shank and Pivotable Retainer.

* cited by examiner

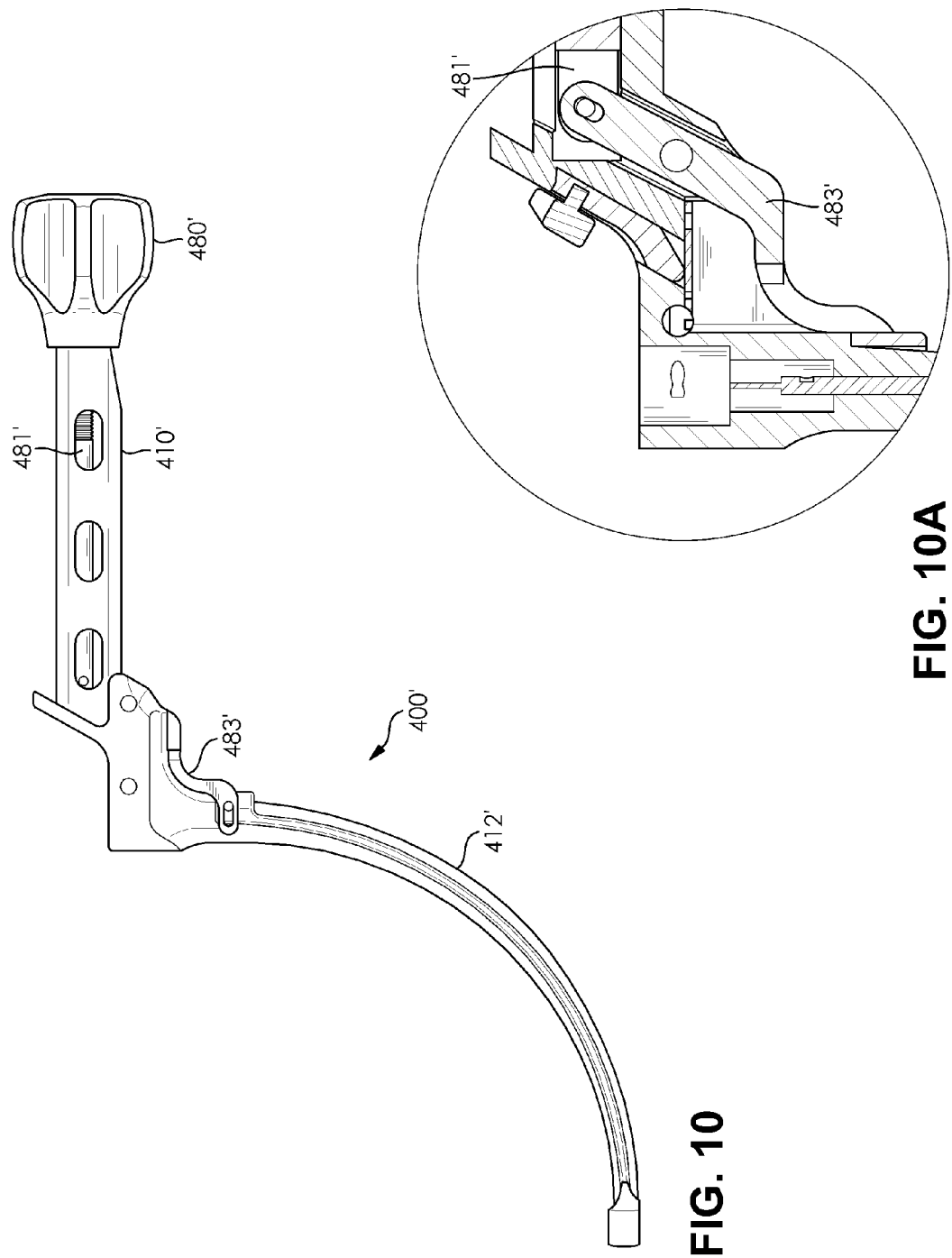

ROD INSERTION TOOLS, RODS AND METHODS

FIELD

The disclosure relates generally to the field of medical devices. More particularly, the disclosure relates to rod insertion tools, rods and methods for placing rods in patients.

BACKGROUND

Over time, bone may degenerate as a result of trauma, disease, and/or natural processes, such as aging. Bone degeneration can affect surrounding tissues and have significant impact on the lifestyle of the patient. For example, destabilization of a spine may result in alteration of a natural spacing between adjacent vertebrae, which can place pressure on nerves that pass between vertebral bodies. Over time, this pressure can cause pain and even permanent nerve damage.

Spinal stabilization procedures are now routinely performed on patients suffering from spinal destabilization. These procedures can be used to maintain and/or re-establish the natural spacing between vertebrae. These procedures can be performed using surgical or recently-developed minimally invasive procedures. Both approaches typically involve the securement of pedicle screws to the pedicles of adjacent vertebrae and placement of a rod between adjacent pedicle screws. The fixed connection between the pedicle screws, and, therefore, between the vertebrae, stabilizes the spacing between the vertebrae. The rod can also be leveraged to compress the vertebrae by reducing the existing spacing between the vertebrae when necessary or desired.

Despite advances in the art, rod placement procedures still face challenges. For example, alignment of rods with pedicle screws, particularly with minimally-invasive procedures and techniques, continues to have a degree of imprecision. Furthermore, current devices fail to provide a sufficiently simple indication of when a rod has been advanced sufficiently. Thus, a need exists for improved rod insertion tools, rods and methods useful in the placement of rods in patients.

BRIEF SUMMARY OF DESCRIBED EMBODIMENTS

Various exemplary rod insertion tools, rods and methods useful for placing rods in patients, such as in the stabilization of the spine of a patient, are described and illustrated herein.

An exemplary rod insertion tool comprises a handle; a main body connected to the handle, the main body having a main body proximal end defining a proximal opening, a main body distal end defining a distal opening, and an inner passageway extending between the proximal and distal openings; a rod engaging member having a rod engaging member proximal end and a rod engaging member distal end, the rod engaging member disposed within the inner passageway and adapted to move from an extended position in which the rod engaging member distal end is disposed outside of the inner passageway to a chambered position in which the rod engaging member distal end is disposed within the inner passageway; and an adjustment mechanism disposed through the proximal opening and operably connected to the rod engaging member proximal end, the adjustment mechanism adapted to cause axial movement of the rod engaging member within the inner passageway upon activation of the adjustment mechanism.

Another exemplary rod insertion tool includes a movable arm attached to the main body. The movable arm is movable between a retracted position on a first side of the main body proximal end and an extended position on a second, opposite side of the main body proximal end.

Another exemplary rod insertion tool includes an outer sheath movable between a retracted position and an extended position and an actuator mechanism operably linked to the outer sheath such that activation of the actuator mechanism causes the outer sheath to move from the retracted position to the extended position.

An exemplary rod has a main body extending between a frustoconical distal end and a rounded frustoconical proximal end and defines an indented faceted surface adjacent the proximal end. The exemplary rod is particularly well-suited for use with the exemplary rod insertion tools.

An exemplary method comprises verifying that each of a movable arm and an outer sheath of an insertion tool according to an embodiment are in their respective retracted position. If one or both of the movable arm and outer sheath is not in its retracted position, an optional step of an exemplary method can comprise placing one or both of the movable arm and outer sheath in its respective retracted position. Another step comprises securing a rod with a rod engaging member of an insertion tool of an embodiment. Another step comprises placing the rod engaging member of the insertion tool in its chambered position. Another step comprises moving the rod through the rod openings of the pedicle screws by moving the insertion tool. Another step comprises moving the movable arm of the insertion tool from its retracted position to its extended position such that the distal end of the movable arm is disposed immediately adjacent a tower to which the first, or proximal, pedicle screw is secured. If compression between the pedicle screws is desired, another step can comprise causing the outer sheath of the insertion tool to move to its extended position such that the distal end of the outer sheath contacts the first tower associated with the first pedicle screw and forces the first pedicle screw to move toward the second pedicle screw.

Additional understanding of the inventive rod insertion tools, rods and methods can be obtained with review of the detailed description, below, and the appended drawings.

BRIEF DESCRIPTION OF THE DRAWINGS

FIG. 10 is a side view of an alternative insertion tool.

FIG. 10A is a partial magnified view of FIG. 10.

DETAILED DESCRIPTION OF ILLUSTRATED EMBODIMENTS

The following detailed description and the appended drawings describe and illustrate various exemplary spinal rod insertion tools, spinal rods and methods for placing spinal rods in a patient. The description and drawings are exemplary in nature and are provided to enable one skilled in the art to make and use one or more exemplary spinal rod insertion tools, spinal rods and/or to practice one or more exemplary methods. They are not intended to limit the scope of the claims in any manner.

Figure 2:
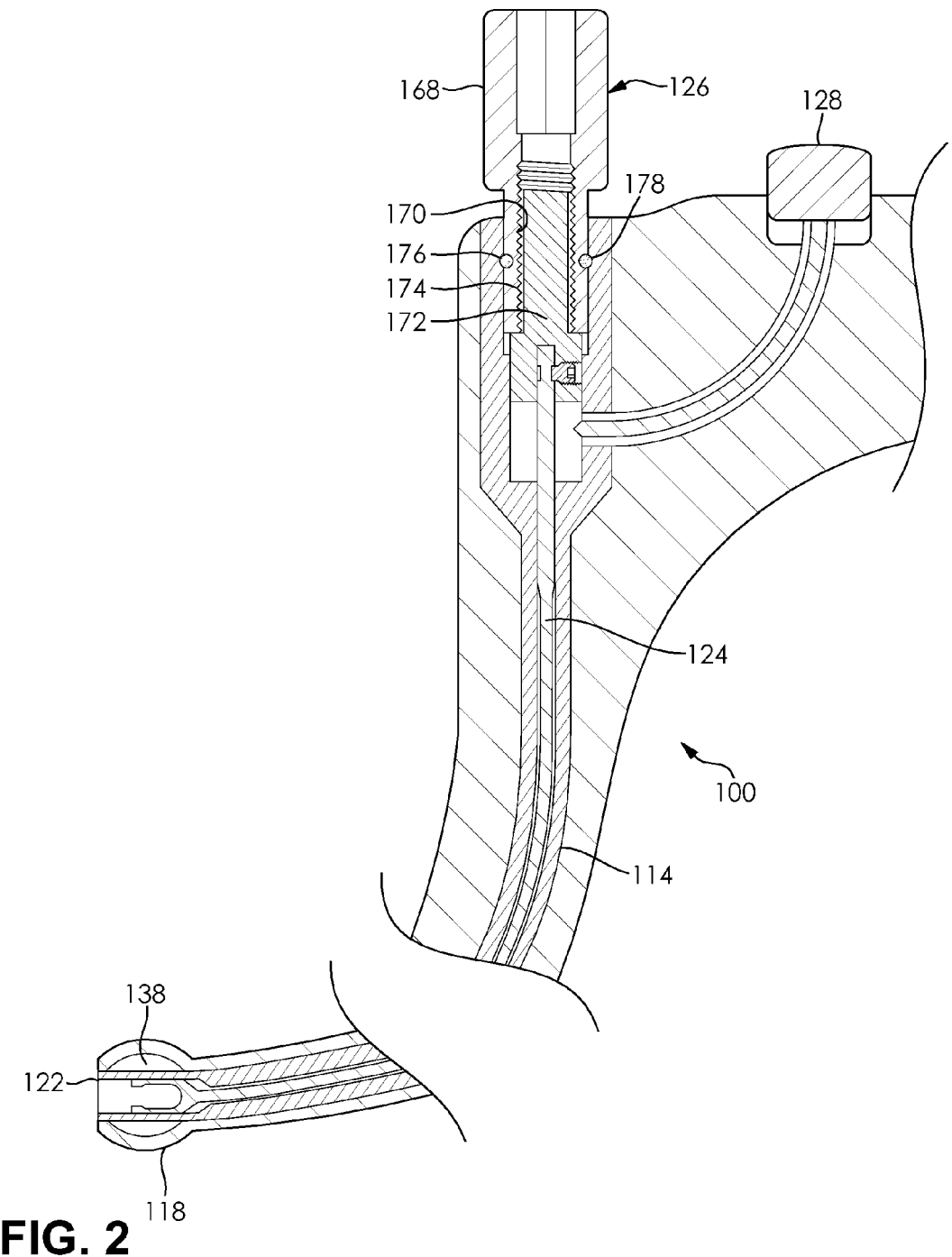
FIG. 2 is a sectional view of the insertion tool illustrated in FIG. 1, taken along line 2-2.
Figure 3:
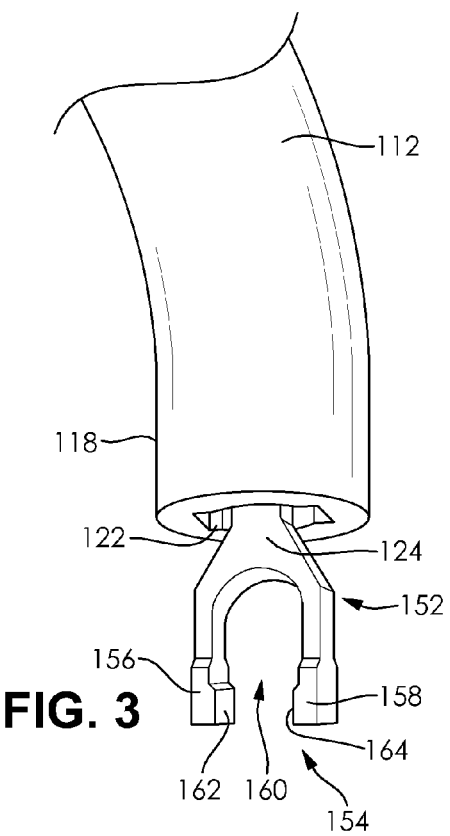
FIG. 3 is a perspective view of the distal end of the insertion tool illustrated in FIG. 1.
Figure 4:
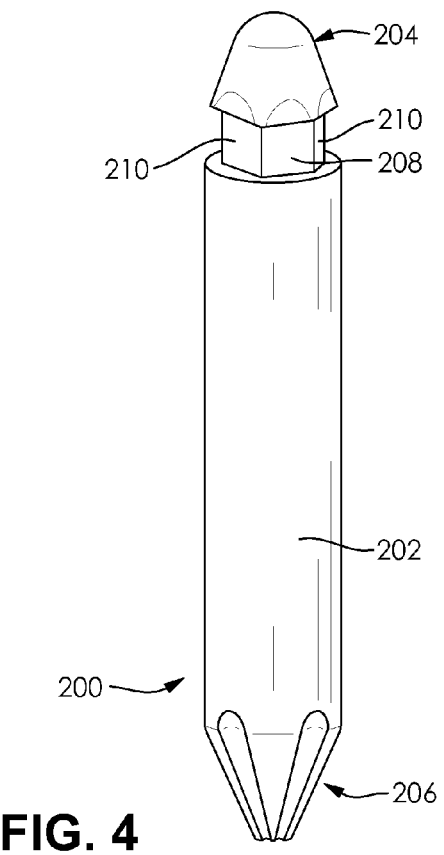
FIG. 4 is a perspective view of an exemplary spinal rod.

FIGS. 1, 2, 3, 5A and 5B illustrate a first exemplary insertion tool 100. FIG. 4 illustrates an exemplary spinal rod 200 suitable for use with the insertion tool 100.

Insertion tool 100 comprises a handle 110 connected to a main body 112. The main body 112 defines an inner passageway 114 that extends between proximal 116 and distal 118 ends of the main body 112. A proximal opening 120 is disposed on the proximal end 116 of the main body 112 and provides communication to the inner passageway 114. Similarly, a distal opening 122 is disposed on the distal end 118 of the main body 112 and provides communication to the inner passageway 114. A rod engaging member 124 is disposed within the inner passageway 114. An adjustment mechanism 126 is operably connected to an end of the rod engaging member 124 and adapted to cause movement of the rod engaging member 124 toward one or both of the proximal 116 and distal 118 ends of the main body 112. A locking mechanism 128 is operably connected to the adjustment mechanism 126 and, when activated, adapted to secure the adjustment mechanism 126 in a position and prevent or substantially prevent movement of the rod engaging member 124 within the inner passageway 114.

The handle 110 need only be a simple member that can be gripped and held by a single human hand. As such, the handle 110 can have any suitable size, shape and configuration. A skilled artisan will be able to select a handle of appropriate size, shape and configuration for an insertion tool according to a particular embodiment based on various considerations, including the intended use of the insertion tool and/or particular needs of the intended users of the insertion tool.

While considered optional, the handle 110 can include various structural elements and/or features that enhance the ergonomic properties of the handle 110 and/or insertion tool 100. For example, the handle 110 can define various indents, ridges, channels, and/or other structures that may facilitate gripping and/or holding of the handle 110 by a user.

The handle 110 can be formed from a single material or from multiple materials. For example, a simple molded plastic part can be used. Alternatively, the handle 110 can comprise a part formed of two or more materials, such as an over-molded part that includes a relatively soft elastomeric grip section 130 disposed on a base section 132 formed of a relatively rigid material, such as a plastic.

The main body 112 can be integrally formed with the handle 110 or can comprise a separate element fixedly connected to the handle 110. In either approach, the main body 112 can be said to be connected to the handle 110, and vice versa.

Figure 1:
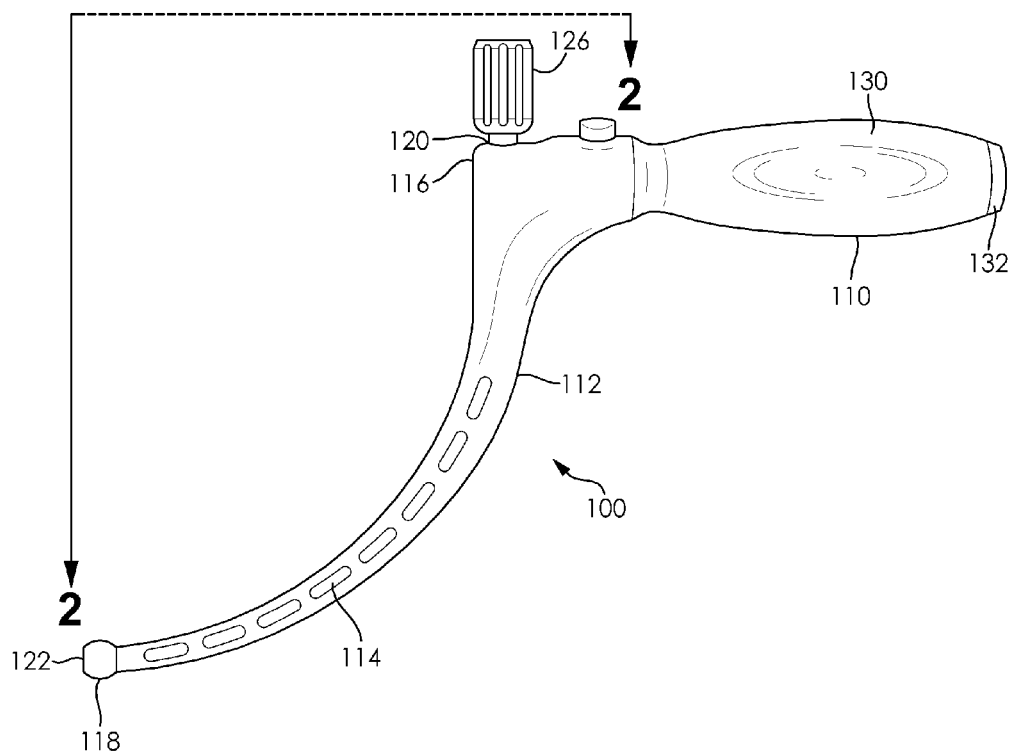
FIG. 1 is a side view of a first exemplary insertion tool.

The main body 112 provides a housing that defines the inner passageway 112 that receives the rod engaging member 124. As such, the main body 112 can have any suitable size, shape and configuration, and need only be capable of receiving the rod engaging member 124 and operating as described herein. A skilled artisan will be able to select an appropriate size, shape and configuration for the main body of an insertion tool according to a particular embodiment based on various considerations, including the intended use of the insertion tool and the patient population with which the insertion tool is intended to be used. As best illustrated in FIGS. 1 and 2, the main body 112 can define a curvilinear shape that positions a first axis $a_1$ extending through the center of the distal opening 122 and a second axis $a_2$ on the same plane and at a right angle with respect to each other. While considered optional, this configuration is considered advantageous at least because it provides a desired clearance and suitable transmission of force for subcutaneous placement of rods with only or substantially only supercutaneous manipulation of the insertion tool 110, as described below. The illustrated configuration also provides desirable performance of the rod engaging member 124, as described below. Other suitable configurations for the main body include linear, substantially linear, angulated, orthogonal, and substantially orthogonal configurations.

The inner passageway 114 is sized and configured to receive the rod engaging member 124 and to allow the slideable movement of the rod engaging member 124 within the passageway, as described below. Thus, the inner passageway 114 can have any suitable size, shape and configuration. A skilled artisan will be able to select an appropriate size, shape and configuration for the inner passageway of an insertion tool according to a particular embodiment based on various considerations, including the size, shape, configuration and material of the associated rod engaging member. Examples of suitable inner passageways include passageways having circular cross-sectional shapes, elliptical cross-sectional shapes, square cross-sectional shapes, cross-sectional shapes of other geometric profiles, inner passageways that have a constant inner diameter or width along their length and inner passageways that have an inner diameter or width that varies along their width, either irregularly, continuously, or intermittently.

The inner passageway 114 in the illustrated insertion tool is exemplary of a suitable inner passageway. In this embodiment, the inner passageway 114 includes a main portion 134, which terminates at the proximal opening 120 at the proximal end 116 of the main body 112, having a circular cross-sectional shape with a constant inner diameter along its length. A distal portion 136, which terminates at the distal opening 122 at the distal end 118 of the main body 112, defines a chamber 138 that has an inner width extending from one portion 140 of the inner wall 142 of the inner passageway 114 to an opposing portion 144 of the inner wall 142 of the inner passageway 114 that is greater than the inner diameter of the main portion 134. As best illustrated in FIG. 3, the chamber 138 advantageously includes one or more additional facets that define a complimentary surface to that of the distal end of an associated rod engaging member 114, as described in detail below. Additionally, the chamber 134 also advantageously includes one or more complimentary surfaces to those defined by a rod with which the insertion tool is intended to be used, such as a conical, substantially conical, frustoconical, or substantially frustoconical surface. For example, as best illustrated in FIG. 3, the chamber 134 in the illustrated embodiment includes a frustoconical inner wall portion 146 adjacent cylindrical inner wall portion 148, which compliments the structure defined by an end of rod 200 illustrated in FIG. 4 (see, for example, FIG. 5B).

The rod engaging member 124 is an elongate member disposed in the inner passageway 114 of the main body 110. The rod engaging member 124 is capable of being moved toward one or the proximal 116 and distal 118 ends of the inner passageway 114 or alternately toward the proximal 116 and distal ends 118 of the inner passageway 114.

The proximal end 150 of the rod engaging member 124 is operably connected to the adjustment mechanism 126, as described below. The distal end 152 defines an engaging structure 154 adapted for holding a rod with which the insertion tool 100 is intended to be used. Any suitable structure can be used for the engaging structure. A skilled artisan will be able to select an appropriate engaging structure for an insertion tool according to a particular embodiment based on various considerations, including the nature, size and configuration of a rod with which the insertion tool is intended to be used. Examples of suitable engaging structures includes a distal portion of the rod engaging member with one or more magnets embedded therein or thereon, a projection adapted to be inserted into a complimentary channel defined by an appropriate rod, and other suitable structures.

The engaging structure 154 included in the illustrated embodiment is an example of a suitable structure for the engaging structure. In this embodiment, the engaging structure 154 includes a pair of opposing arms 156, 158 that define an internal notch, such as u-shaped notch 160. A first shoulder 162 projects inwardly into the u-shaped notch 160 from the first arm 156 and defines a first mating surface 164. Similarly, a second shoulder 166 projects inwardly into the u-shaped notch 160 from the second arm 158 and defines a second mating surface 166. The first 164 and second 166 mating surfaces are complimentary to surfaces 206 defined by a rod intended to be used with the insertion tool 100, such as rod 200 illustrated in FIG. 4. The arms 156, 158 are sufficiently resilient to allow an end of the rod 200 to be passed into the u-shaped notch 160 until the mating surfaces 164, 166 interface with complimentary mating surfaces 210 on the rod 200.

Figure 5A:
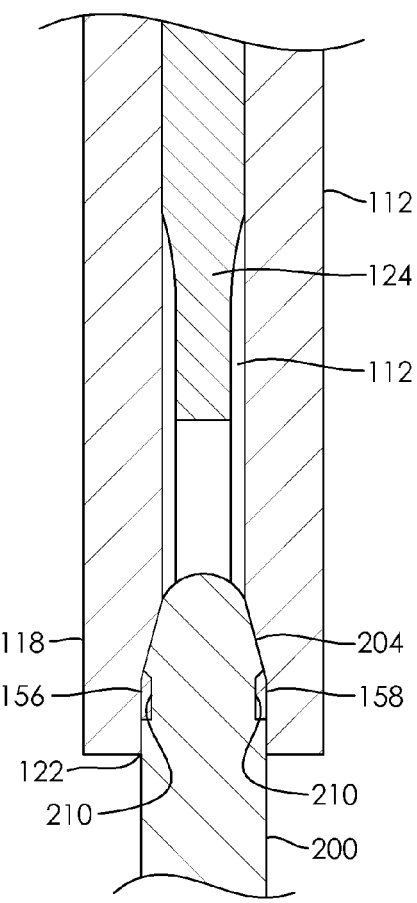
FIG. 5A is a sectional view of the distal end of the insertion tool illustrated in FIG. 1, with an engaged spinal rod. The insertion tool is in a first, extended configuration.
Figure 5B:
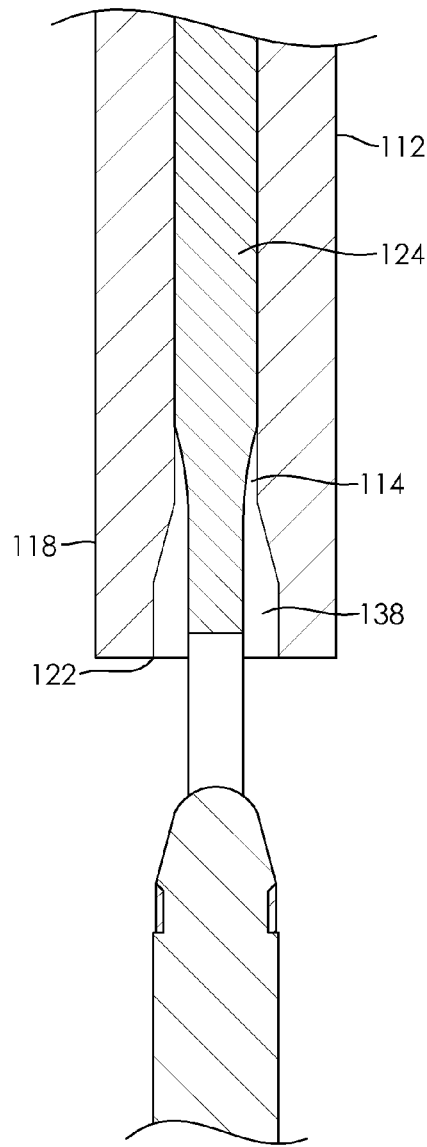
FIG. 5B is a sectional view of the distal end of the insertion tool illustrated in FIG. 1, with an engaged spinal rod. The insertion tool is in a second, retracted configuration.

As best illustrated in FIGS. 3, 5A and 5B, the rod engaging member 124 is advantageously movable between an extended position, illustrated in FIGS. 3 and 5A, in which the distal end 152, and the engaging structure 154, of the rod engaging member 124 are disposed distal to and outside of the chamber 138 of the inner passageway 114, and a chambered position, illustrated in FIG. 5B, in which the distal end 152 of the rod engaging member 124 is disposed within the chamber 138 of the rod engaging member 124.

The adjustment mechanism 126 is operably connected to the rod engaging member 124 such that activation of the adjustment mechanism, accomplished through appropriate action, causes axial movement of the rod engaging member 124 within the inner passageway 114. For example, in the illustrated embodiment, the adjustment mechanism 126 is a rotatable knob that is operably connected to the rod engaging member 124 through complimentary mating threads. For the illustrated embodiment, clockwise rotation of the adjustment mechanism 126 results in axial movement of the rod engaging member 124 toward the distal end 118 of the inner passageway 114, while counter-clockwise rotation of the adjustment mechanism 126 results in axial movement of the rod engaging member 124 toward the proximal end 116 of the inner passageway 114. In use, the adjustment mechanism 126 of the illustrated insertion tool 100 can be rotated clockwise to cause rod engaging member 124 to move to the extended position in which the distal end 152 and the engaging structure 154 are disposed distal to and outside of the chamber 138. This can be performed prior to and in preparation for engagement with a rod. Subsequently, the adjustment mechanism 126 can be rotated counter-clockwise to cause the rod engaging member 124, with or without an engaged rod, to move to the chambered position in which the distal end 152 and the engaging structure 154 are disposed within the chamber 138. The adjustment mechanism can also be configured to operate in an opposite manner, e.g., counter-clockwise rotation to move the rod engaging member 124 to the extended position and clockwise rotation to cause the rod engaging member 123 to move to the chambered position.

Any suitable structure can be used for the adjustment mechanism 126 and a skilled artisan will be able to select an appropriate structure for an insertion tool according to a particular embodiment based on various considerations, including the size and configuration of the main body 112 and inner passageway 114, and any preferences for the type of motion by an intended user of the insertion tool to effect movement of the rod engaging member 124. The illustrated adjustment mechanism 126 provides an example of a suitable structure. In the illustrated embodiment, the adjustment mechanism 126 defines an external knob 168 and an internal thread 170. An internal threaded member 172 defines a complimentary external thread 174 that interfaces with the internal thread 170 of the adjustment mechanism 126 and is fixedly secured to the proximal end 150 of the rod engaging member 124. Alternatively, the internal threaded member 172 can be integrally formed by the proximal end 150 of the rod engaging member 124. The adjustment mechanism 126 is fixed in position, such as by retaining rods 176, 178, such that rotation of knob 168 results in linear movement of the internal threaded member 172 and, as a result, of the attached rod engaging member 124.

A locking mechanism 128 is operably connected to the adjustment mechanism 126 and, when activated, adapted to secure the adjustment mechanism 126 in a position and prevent or substantially prevent movement of the rod engaging member 124 within the inner passageway 114 For example, in the illustrated embodiment, the locking mechanism 128 is a depressable button that attached or formed with a shaft member. Upon depression of the button, the locking mechanism effectively secure the adjustment mechanism 126 as a portion of the shaft member projects into a portion of the inner passageway 114 to prevent distally-directed movement of the rod engaging member 124 beyond a particular point. Alternatively, the shaft member can project into a portion of the rod engaging member 124 or attached structure such that the locking mechanism 128 prevents any further movement, distally-directed or proximally-directed, upon activation, such as by depression of the illustrated button.

Any suitable structure can be used for the locking mechanism 128 and a skilled artisan will be able to select an appropriate structure for an insertion tool according to a particular embodiment based on various considerations, including the size and configuration of the main body 112 and inner passageway 114, and any preferences for the type of motion by an intended user of the insertion tool to effect prevention of movement of the rod engaging member 124. The illustrated locking mechanism 128 provides an example of a suitable structure.

FIG. 4 illustrates an exemplary spinal rod 200 suitable for use with the insertion tools and methods, including insertion tool 100 described above. Rod 200 is an elongate member comprising a main body 202 extending between proximal 204 and distal 206 ends. The main body 202 is substantially cylindrical in shape. The distal end 206 is frustoconical in shape. The proximal end 204 includes a rounded frustoconical shape. An indented faceted surface 208 is disposed adjacent the proximal end 204. The indented faceted surface has a reduced outer diameter as compared to that of the main body and defines a series of surfaces, including the mating surfaces 210 that interface with the mating surfaces 164, 166 of the arms 156, 158 of the rod engaging member 124 during use of the insertion tool 100.

Figure 6A:
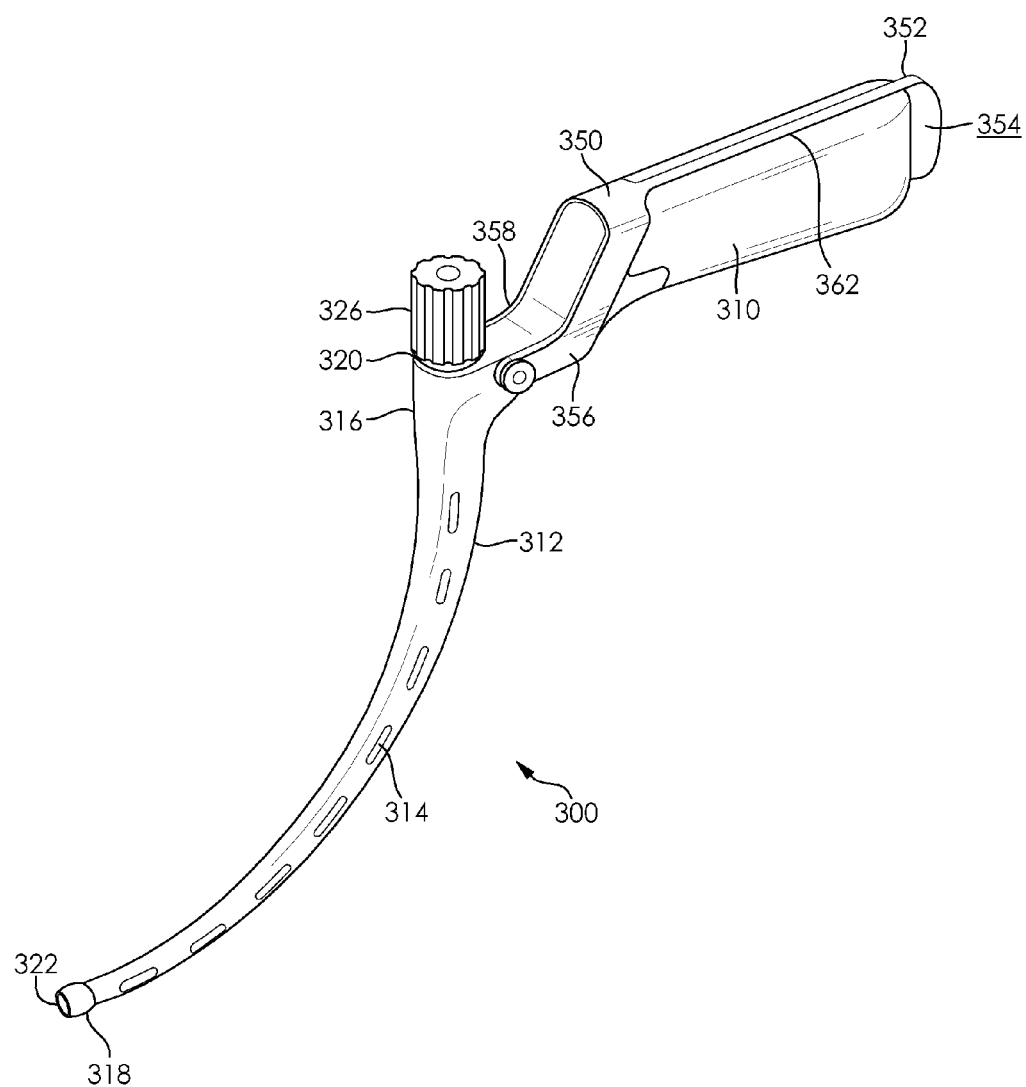
FIG. 6A is a perspective view of a second exemplary insertion tool. The insertion tool has a movable arm in a first, retracted configuration.
Figure 6B:
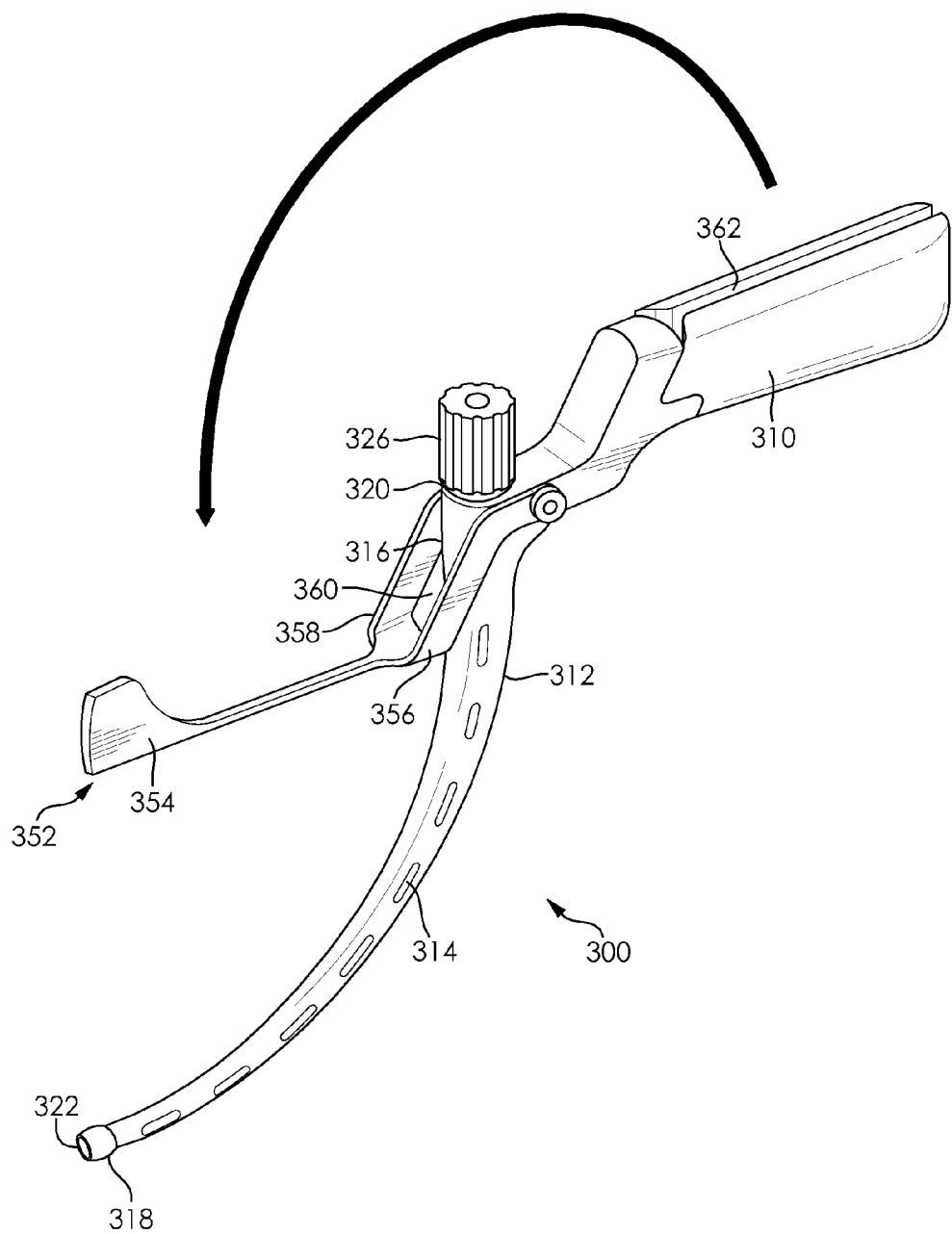
FIG. 6B is a perspective view of the insertion tool illustrated in FIG. 6A. The insertion tool has a movable arm in a second, extended configuration.

FIGS. 6A and 6B illustrate a second exemplary insertion tool 300. The insertion tool 300 is similar to the insertion tool 100 described above and illustrated in FIGS. 1, 2, 3, 5A and 5B, except as described below. Thus, insertion tool 300 comprises a handle 310 connected to a main body 312. The main body 312 defines an inner passageway 314 that extends between proximal 316 and distal 318 ends of the main body 312. A proximal opening 320 is disposed on the proximal end 316 of the main body 312 and provides communication to the inner passageway 314. Similarly, a distal opening 322 is disposed on the distal end 318 of the main body 312 and provides communication to the inner passageway 314. A rod engaging member 324 is disposed within the inner passageway 314. An adjustment mechanism 326 is operably connected to an end of the rod engaging member 324 and adapted to cause movement of the rod engaging member 124 toward one or both of the proximal 316 and distal 318 ends of the main body 312.

In this embodiment, insertion tool 300 includes a movable arm 350 attached to the main body 312. The movable arm 350 is movable between a retracted, or seated, position, illustrated in FIG. 6A, in which the movable arm 350 is disposed adjacent the handle 310 relative to the proximal end 316 of the main body 312, and an extended position, illustrated in FIG. 6B, in which the movable arm 350 is disposed opposite the handle 310 relative to the proximal end 316 of the main body 312. Any suitable structure and attachment can be used for the movable arm, and a skilled artisan will be able to select an appropriate structure for a movable arm in an insertion tool according to a particular embodiment based on various considerations, including the size, shape and configuration of the main body and/or handle of the insertion tool. The illustrated movable arm 350 is an example of a suitable structure. In this embodiment, the movable arm 350 comprises a distal end 352 that forms a paddle surface 354, a pair of opposing arms 356, 358 that, together, define the proximal end 360 of the movable arm 350 and that are each attached to the main body 312 of the insertion tool 300, such as by rod 362. The opposing arms 356, 358 define an interior space 360 that allows the adjustment mechanism 326 to pass through when the movable arm 350 is moved from the retracted position to the extended position. Also in the illustrated embodiment, the handle 310 defines a channel 362 that receives the main body 364 and paddle surface 354 of the movable arm 350 when the movable arm 350 is in the retracted position.

As best illustrated in FIG. 6B, the movable arm 350 moves from the retracted position to the extended position along a plane that also includes the central longitudinal axis of the main body 312 of the insertion tool 300. Inclusion of a movable arm, such as movable arm 350 in the illustrated embodiment, is considered advantageous at least because the movable arm 350 can provide a physical barrier to continued forward movement of the insertion tool 300 and an engaged rod during use once a desired positioning has been achieved, such as when the distal end 352 contacts a tower associated with a pedicle screw through which the associated rod is being placed. Furthermore, when positioned in the extended position, the movable arm 350 can provide guidance to a user of the insertion tool 300 as to the direction and/or location of an associated rod.

Figure 7:
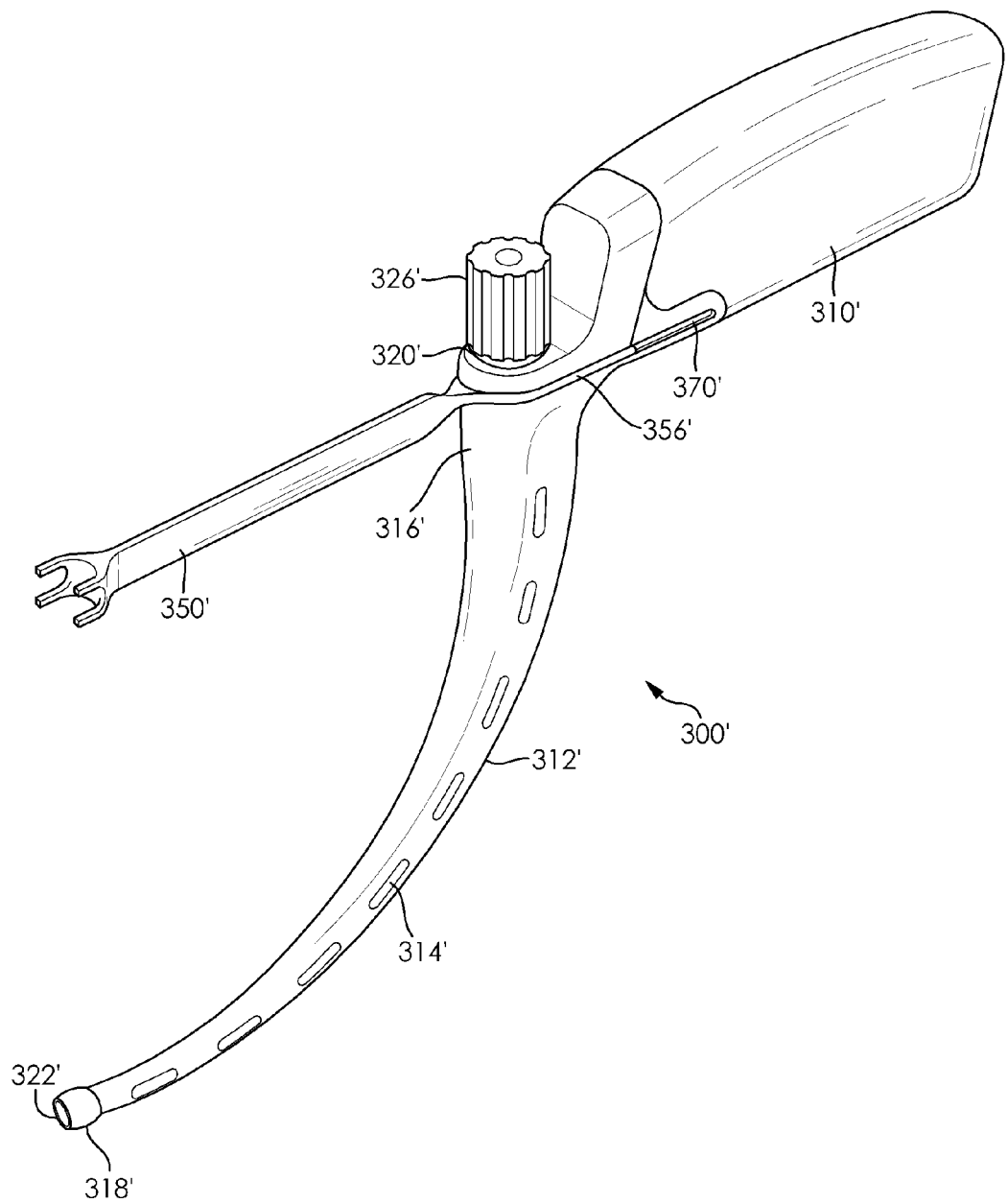
FIG. 7 is a perspective view of an alternative insertion tool.
Figure 8:
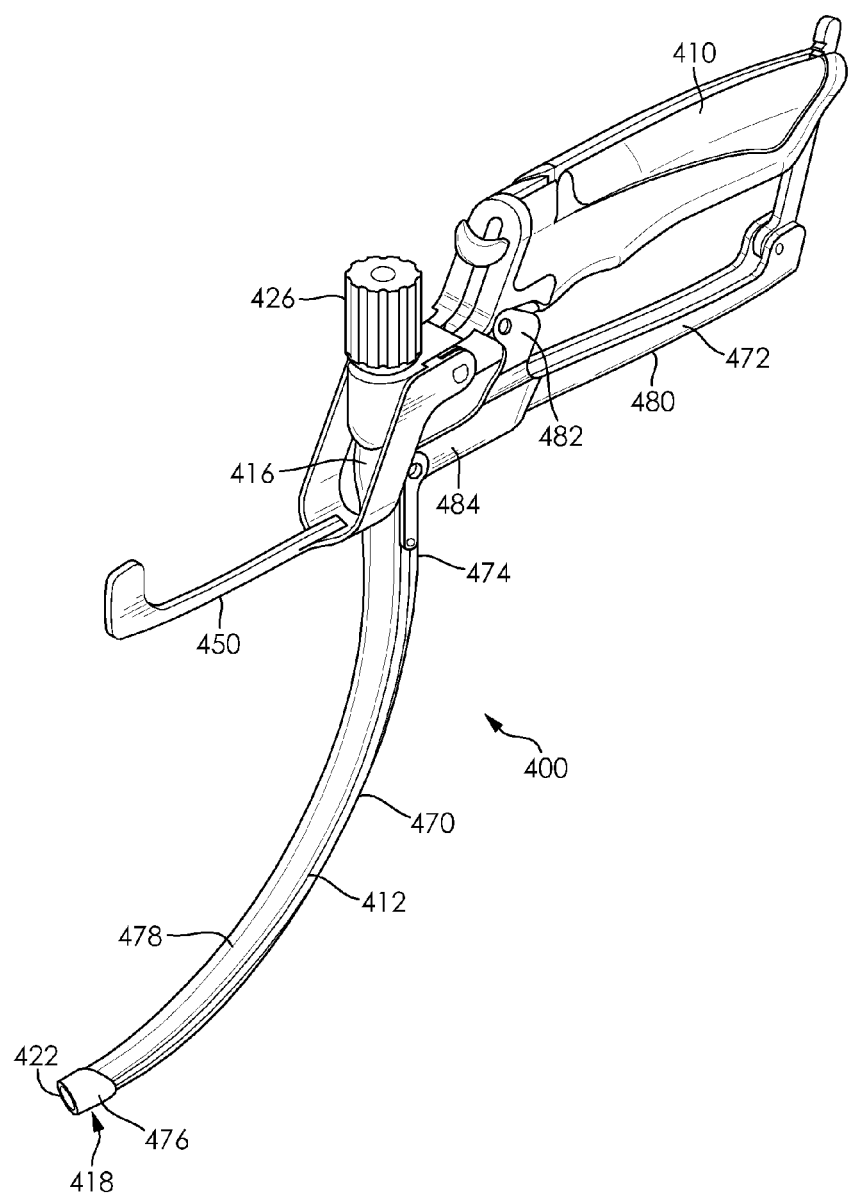
FIG. 8 is a perspective view of a third alternative insertion tool.

FIG. 7 illustrates an alternative insertion tool 300'. The insertion tool 300' is similar to the insertion tool 300 described above and illustrated in FIGS. 6A and 6B, except as described below. Thus, insertion tool 300' comprises a handle 310' connected to a main body 312'. The main body 312' defines an inner passageway 314' that extends between proximal 316' and distal 318' ends of the main body 312'. A proximal opening 320' is disposed on the proximal end 316' of the main body 312' and provides communication to the inner passageway 314'. Similarly, a distal opening 322' is disposed on the distal end 318' of the main body 312' and provides communication to the inner passageway 314'. A rod engaging member 324' is disposed within the inner passageway 314'. An adjustment mechanism 326' is operably connected to an end of the rod engaging member 324' and adapted to cause movement of the rod engaging member 124' toward one or both of the proximal 316' and distal 318' ends of the main body 312'.

In this embodiment, a modular arm 350' is used in place of the movable arm 350 of the embodiment illustrated in FIGS. 6A and 6B. The modular arm 350' defines a pair of opposing arms 356', 358' that can be received by complimentary slots 370', 372' defined by the main body 312' of the insertion tool 300. The modular arm 350' is used in similar fashion and for similar purpose as the movable arm 350 of the insertion tool 300 illustrated in FIGS. 6A and 6B, except that instead of being rotated from the retracted position to the extended position, the modular arm 350' is moved from an unattached position, in which it is not connected to the insertion tool 300', to an attached position, illustrated in FIG. 7, in which the opposing arms 356', 358' are seated in the slots 370', 372' of the main body 312'. Also, the distal end 352' of the modular arm 350' defines an alternate structure having multiple u-shaped channels suitable for contacting and/or interfacing with towers associated with one or more pedicle screwes through which an engaged rod is being passed.

FIGS. 8, 9A, 9B, and 9C illustrate a third exemplary insertion tool 400. The insertion tool 400 is similar to the insertion tool 300 described above and illustrated in FIGS. 6 and 6A, except as described below. Thus, insertion tool 400 comprises a handle 410 connected to a main body 412. The main body 412 defines an inner passageway 414 that extends between proximal 416 and distal 418 ends of the main body 412. A proximal opening 420 is disposed on the proximal end 416 of the main body 412 and provides communication to the inner passageway 414. Similarly, a distal opening 422 is disposed on the distal end 418 of the main body 412 and provides communication to the inner passageway 414. A rod engaging member 424 is disposed within the inner passageway 414. An adjustment mechanism 426 is operably connected to an end of the rod engaging member 424 and adapted to cause movement of the rod engaging member 424 toward one or both of the proximal 416 and distal 418 ends of the main body 412. A movable arm 450 is attached to the main body 412 and is movable between a retracted position, illustrated in FIG. 9A, in which the movable arm 450 is disposed adjacent the handle 410 relative to the proximal end 416 of the main body 412, and an extended position, illustrated in FIGS. 8, 9B and 9C, in which the movable arm 450 is disposed opposite the handle 410 relative to the proximal end 416 of the main body 412.

In this embodiment, insertion tool 400 includes an outer sheath 470 disposed along the external surface of the main body 412 and an actuator mechanism 472 operably linked to the outer sheath 470. The outer sheath 470 has a proximal end 474 and a distal end 476 and extends between the proximal 474 and distal 476 ends along a length of the main body 412. The outer sheath 470 is movable between a retracted position and an extended position. In the retracted position, illustrated in FIGS. 8, 9A and 9B, the distal end 476 is disposed in either a flush arrangement with the distal end 418 of the main body 412 or proximal to the distal end 418 of the main body 412. In the extended position, illustrated in FIG. 9C, the distal end 476 is disposed distal to the distal end 418 of the main body 412. As such, the distal end 476 of the outer sheath 470 extends axially beyond the distal end 418 of the main body when the outer sheath 470 is in the extended position. The actuator mechanism 472 is operably linked to the outer sheath 470 such that activation of the actuator mechanism 472 causes the outer sheath 470 to move from the retracted position to the extended position.

Figure 9A:
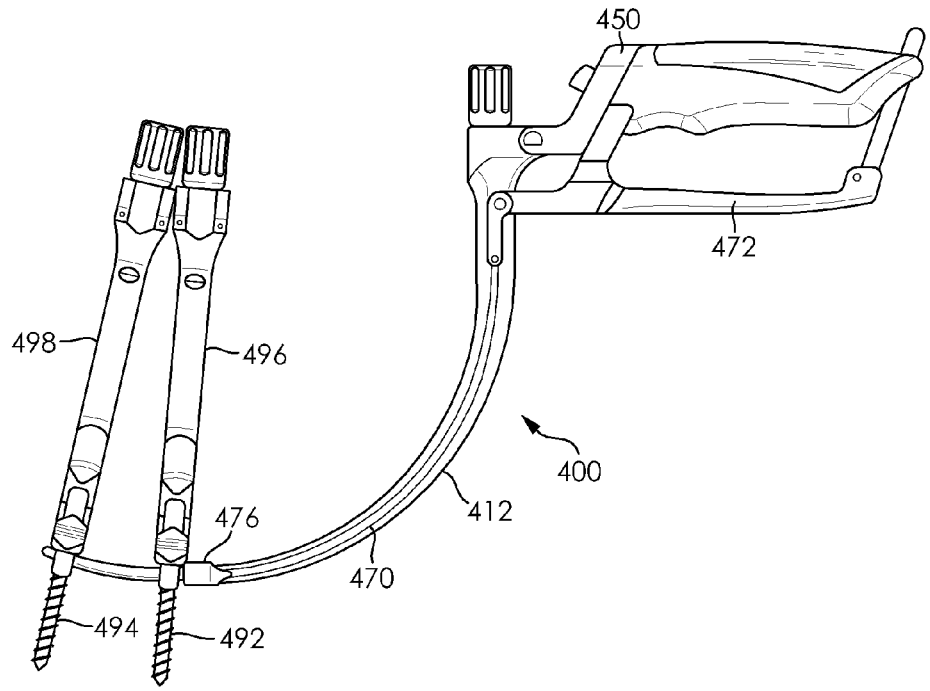
FIG. 9A is a side view of the insertion tool illustrated in FIG. 8 with an engaged spinal rod and associated towers. The insertion tool is shown in a first configuration with a movable arm in a first, retracted configuration and a compressor sheath in a first, retracted configuration.
Figure 9B:
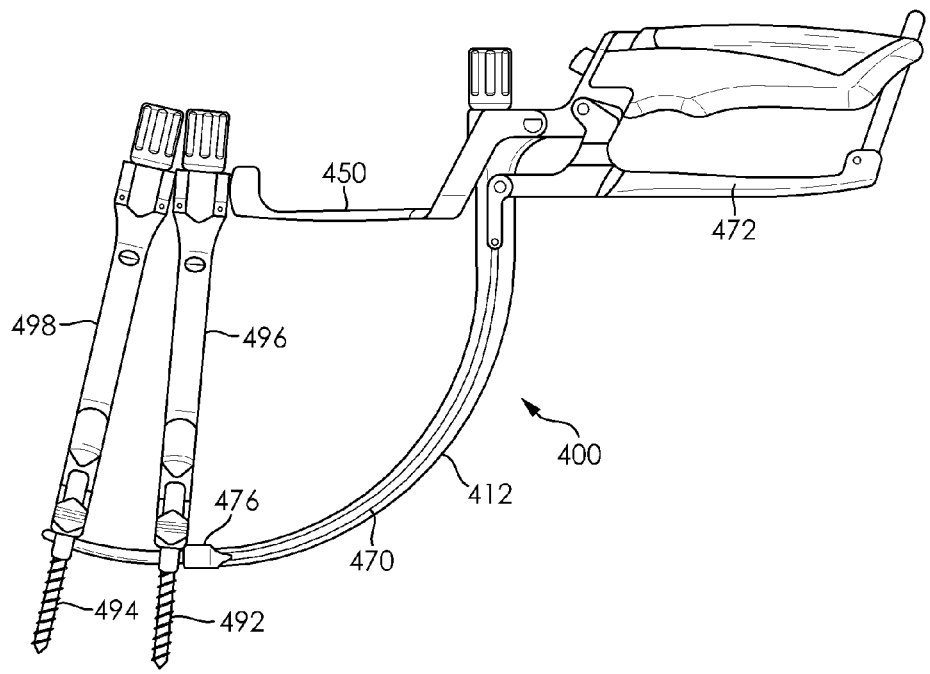
FIG. 9B is a side view of the insertion tool illustrated in FIG. 9A. The insertion tool is shown in a second configuration with a movable arm in a second, extended configuration and a compressor sheath in a first, retracted configuration.
Figure 9C:
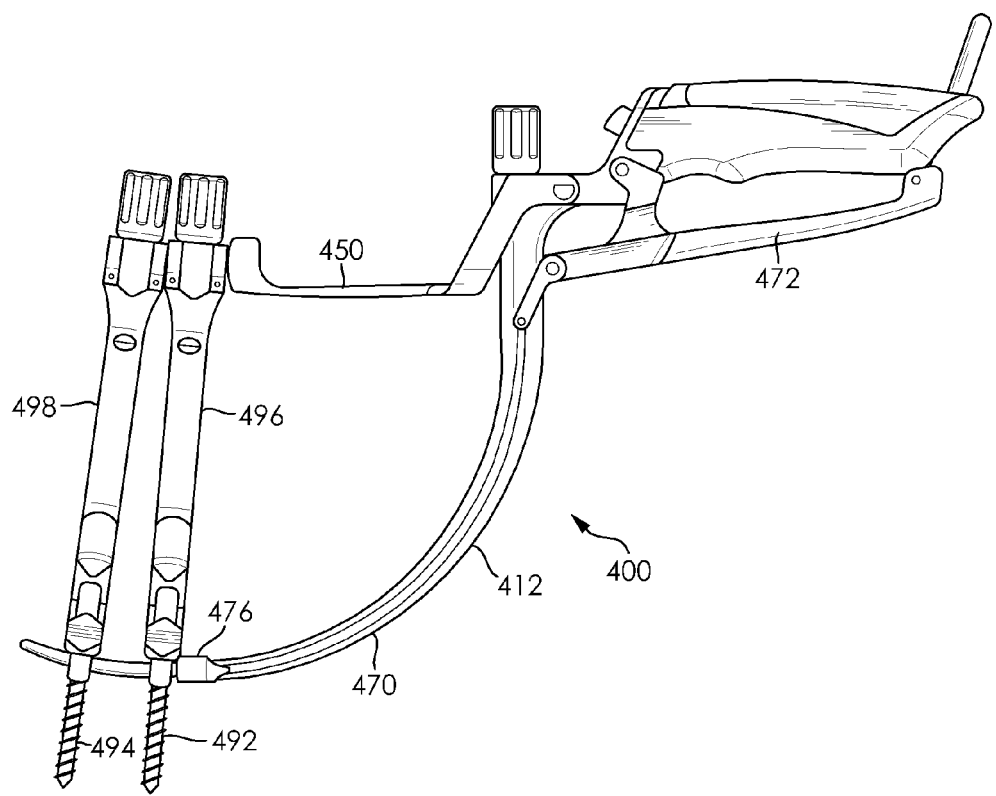
FIG. 9C is a side view of the insertion tool illustrated in FIGS. 9A and 9B. The insertion tool is shown in a third configuration with a movable arm in a second, extended configuration and a compressor sheath in a second, extended configuration.
Figures 11, 11A:
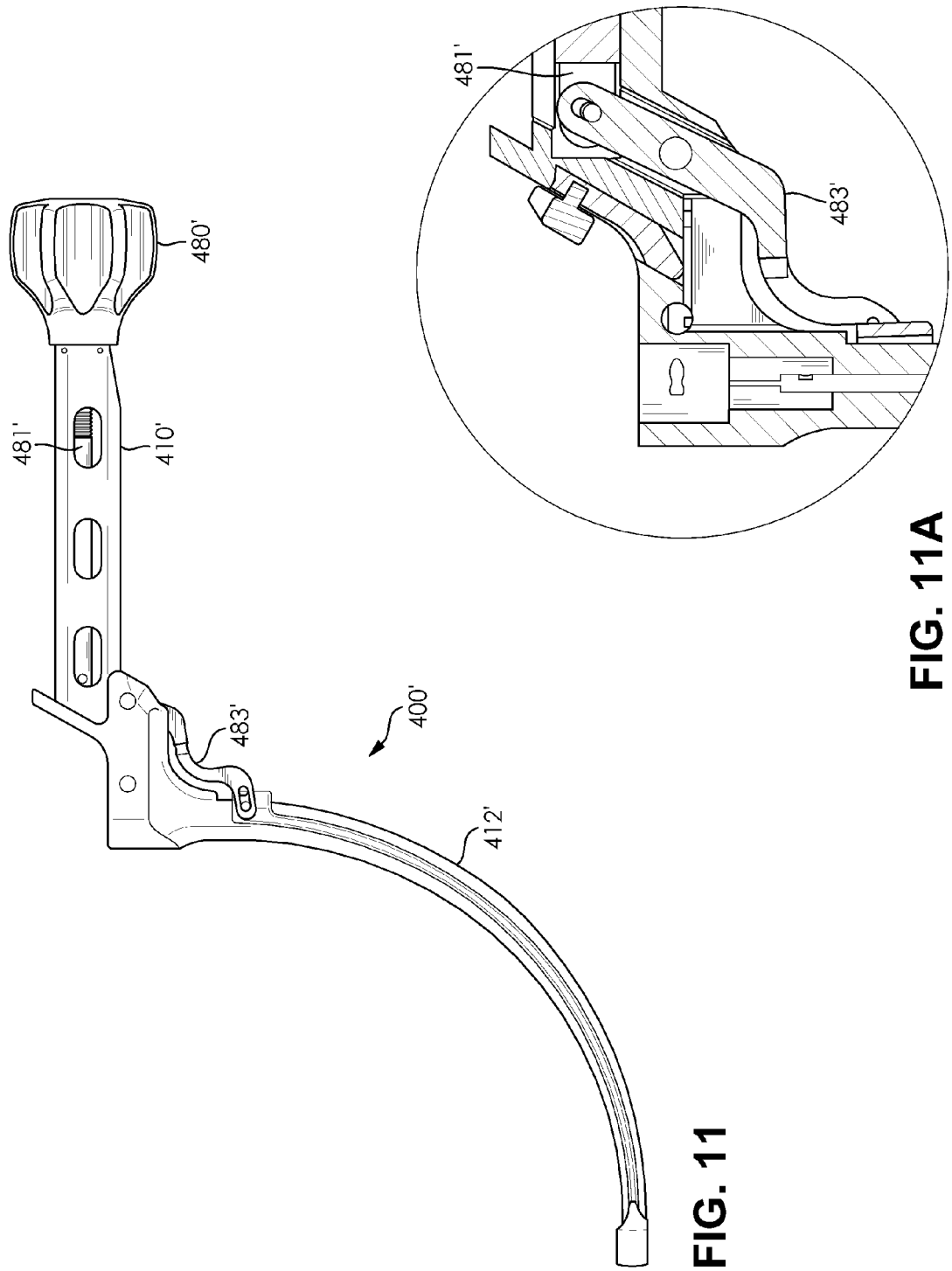
FIG. 11 is another side view of the insertion tool illustrated in FIG. 10.
FIG. 11A is a partial magnified view of FIG. 11.

FIGS. 9A through 9C illustrate the insertion tool 400 in various configurations that the insertion tool 400 adopts during various stages of use. In these figures, the insertion tool 400 is being used to place a spinal rod 490 through first 492 and second 494 pedicle screws. In each of these figures, the insertion tool 400 is illustrated with the spinal rod 490 engaged, i.e., the rod engaging member 424 is in the chambered position such that the rod 400 is secured within the distal opening 422, and passed through the rod openings of the pedicle screws 492, 494. Also, the pedicle screws 492, 494 are secured to their associated placement towers 496, 498. In FIG. 9A, the insertion tool 400 is shown in a first configuration. Each of the movable arm 450 and the outer sheath 470 is in its respective retracted position. The rod 490 is disposed through the rod openings of the pedicle screws 492, 494. To ensure that additional and/or unnecessary forward movement of the rod 490 is not produced, a user can place the insertion tool 400 into the configuration illustrated in FIG. 9B. Here, the movable arm 450 has been moved from its retracted position to its extended position. The distal end 452 of the movable arm 450 is disposed immediately adjacent the first tower 496 that to which the first, or proximal, pedicle screw 492 is secured. In this configuration, the movable arm 450 provides a physical barrier that prevents additional forward movement of the insertion tool 400, and the engaged rod 490. As best illustrated in FIG. 9B, rod 490 can be selected to have an appropriate length that ensures a sufficient length of the rod has passed through each of the pedicle screws 492, 494, or any appropriate number of pedicle screws, when the movable arm 450 contacts or nearly contacts the first tower 496 associated with the first pedicle screw 492. If compression between the pedicle screws 492, 494 is desired, a user can place the insertion tool 400 into the configuration illustrated in FIG. 9C. Here, the actuator mechanism 472 has been activated, causing the outer sheath 470 to move to its extended position. By moving from its retracted position to its extended position, the distal end 476 of the outer sheath 470 has moved axially beyond the distal end 418 of the main body 412 to contact the first tower 496 associated with the first pedicle screw 492. Once contact between these elements is achieved and the outer sheath 490 continues movement toward its extended position, the outer sheath 470 forces the first tower 496 and first pedicle screw 492 to move toward the second tower 498 and the second pedicle screw 494. This reduces the axial length between the towers 496, 498, pedicle screws 492, 494 and the vertebrae to which they have been secured, thereby achieving the desired compression.

Any suitable structure can be used for the outer sheath, and a skilled artisan will be able to select an appropriate structure for an outer sheath in an insertion tool according to a particular embodiment based on various considerations, including the size, shape and configuration of the main body. The structure selected need only be able to perform as described. The illustrated outer sheath 470 is an example of a suitable structure. In this embodiment, the outer sheath 470 comprises an elongate member disposed around the main body 412. The distal end 476 of the outer sheath 470 defines a cylindrical portion that extends around the entire circumference of the main body 412. Along a significant portion of its length, though, the outer sheath 470 defines a window 476 through which the main body 412 is accessible. As illustrated, the window 476 is advantageously positioned along an inner curve of the main body 412 in the illustrated embodiment, while the material of the outer sheath 470 along the length defining the window 478 is disposed along the outer curve of the main body 412. Other examples of suitable structures for an outer sheath include an elongate, continuous tubular member. Alternatively, instead of having a portion that extends around a circumference of the main body, a solid member, such as a wire or rod, can be placed along a length of the main body.

Any suitable structure can be used for the actuator mechanism, and a skilled artisan will be able to select an appropriate structure for an actuator mechanism in an insertion tool according to a particular embodiment based on various considerations, including the size, shape and configuration of the outer sheath and the main body in the insertion tool. The illustrated actuator mechanism is an example of a suitable structure. In this embodiment, the actuator mechanism 472 includes a grip 480 that is pivotably mounted to the main body 412 at pivot connection 482 and attached to the proximal end 474 of the outer sheath 470 through grip extension 484. When the grip 480 is brought closer to the handle 410 of the insertion tool 400, it pivots on pivot connection 482 such that the grip 480 moves toward the handle 410 and the grip extension 484 moves away from the handle 410. By way of its attachment to grip extension 484, the proximal end 474 of the outer sheath 470 moves downward with respect to the main body 412 as a result of the upward movement of grip 480. In turn, this forces the outer sheath 470 to move to its extended position, placing its distal end 476 axially beyond the distal end 418 of the main body 412. A connector, such as ratchet mechanism 486, can extend between the grip 480 and the handle 410 to prevent premature, reverse, or other undesired movement of grip 480 and, therefore, outer sheath 470.

FIG. 10 illustrates an alternative insertion tool 400'. The insertion tool 400' is similar to the insertion tool 400 described above and illustrated in FIGS. 8, 9A, 9B, and 9C, except as described below. Thus, insertion tool 400' comprises a handle 410' connected to a main body 412'. The main body 412' defines an inner passageway 414' that extends between proximal 416' and distal 418' ends of the main body 412'. A proximal opening 420' is disposed on the proximal end 416' of the main body 412' and provides communication to the inner passageway 414'. Similarly, a distal opening 422' is disposed on the distal end 418' of the main body 412' and provides communication to the inner passageway 414'. A rod engaging member 424' is disposed within the inner passageway 414'. An adjustment mechanism 426' is operably connected to an end of the rod engaging member 424' and adapted to cause movement of the rod engaging member 424' toward one or both of the proximal 416' and distal 418' ends of the main body 412'.

In this embodiment, insertion tool 400' includes a knob 480' with an extension rod 481' that is connected to pivot arm 483'. When the knob 480' is rotated, pivot arm 483' pivots on pivot connection 482' such that pivot arm extension 484' moves away from the handle 410'. By way of its attachment to pivot arm extension 484', the proximal end 474' of the outer sheath 470' moves downward with respect to the main body 412' as a result of the rotational movement of knob 480'. In turn, this forces the outer sheath 470' to move to its extended position, placing its distal end 476' axially beyond the distal end 418' of the main body 412'.

The insertion tools described herein can be used in the placement of rods in patients. For example, the insertion tools can be used in the placement of a spinal rod through first and second pedicle screws that have been secured to vertebrae of a patient. Accordingly, methods of using the insertion tools are also contemplated. As described above, an exemplary method comprises verifying that each of a movable arm and an outer sheath of an insertion tool according to an embodiment are in their respective retracted position. If one or both of the movable arm and outer sheath is not in its retracted position, an optional step of an exemplary method can comprise placing one or both of the movable arm and outer sheath in its respective retracted position. Another step of an exemplary method comprises securing a rod with a rod engaging member of an insertion tool of an embodiment. Another step of an exemplary method comprises placing the rod engaging member of the insertion tool in its chambered position. Another step of an exemplary method comprises moving the rod through the rod openings of the pedicle screws by moving the insertion tool. Another step of the exemplary method comprises moving the movable arm of the insertion tool from its retracted position to its extended position such that the distal end of the movable arm is disposed immediately adjacent a tower to which the first, or proximal, pedicle screw is secured. If compression between the pedicle screws is desired, another step of an exemplary method can comprise causing the outer sheath of the insertion tool to move to its extended position such that the distal end of the outer sheath contacts the first tower associated with the first pedicle screw and forces the first pedicle screw to move toward the second pedicle screw.

Another exemplary method comprises verifying that a movable arm of an insertion tool according to an embodiment is in its retracted position. If the movable arm is not in its retracted position, an optional step of an exemplary method can comprise placing the movable arm in its respective retracted position. Another step of an exemplary method comprises securing a rod with a rod engaging member of an insertion tool of an embodiment. Another step of an exemplary method comprises placing the rod engaging member of the insertion tool in its chambered position. Another step of an exemplary method comprises moving the rod through the rod openings of the pedicle screws by moving the insertion tool. Another step of the exemplary method comprises moving the movable arm of the insertion tool from its retracted position to its extended position such that the distal end of the movable arm is disposed immediately adjacent a tower to which the first, or proximal, pedicle screw is secured.

Another exemplary method comprises moving the movable arm of an insertion tool according to an embodiment from its retracted position to its extended position prior to a step of moving a rod through rod openings of the pedicle screws. Another step of an exemplary method comprises securing a rod with a rod engaging member of the insertion tool. Another step of an exemplary method comprises placing the rod engaging member of the insertion tool in its chambered position. Another step of an exemplary method comprises moving the rod through the rod openings of the pedicle screws by moving the insertion tool. In this step, the movable arm, which is in its extended position, can be used as a visual or other guide for the movement of the insertion tool and, therefore, the attached rod. Another step of the exemplary method comprises continuing the step of moving the rod through the rod openings until the distal end of the movable arm is disposed immediately adjacent a tower to which the first, or proximal, pedicle screw is secured.

Each of the elements of the insertion tools and spinal rods can be made from any suitable material and a skilled artisan will be able to select appropriate materials for an insertion tool according to a particular embodiment based on various considerations, including the desired properties of each element. Conventional materials currently used in similar devices are considered suitable, as are materials developed subsequent to this disclosure and accepted as suitable for use in similar devices. Examples of suitable materials for various elements of the insertion tools and spinal rods include, but are not limited to, titanium, titanium alloys, stainless steel, ceramics, and polymeric materials. The insertion tools and spinal rods can be autoclaved, chemically sterilized, or otherwise treated in preparation for use in a surgical and/or minimally-invasive procedure, which should be considered when selecting appropriate materials.

The foregoing detailed description refers to exemplary rod insertion tools, rods and methods and includes the best mode for practicing the invention. The description and the appended drawings illustrating the described rod insertion tools, rods and methods are intended only to provide examples and not to limit the scope of the claims in any manner.

What is claimed is:

1. A rod insertion tool, comprising:
   a handle;
   a main body connected to the handle, the main body having a main body proximal end defining a proximal opening, a main body distal end defining a distal opening, and an inner passageway extending between the proximal and distal openings;
   a rod engaging member having a rod engaging member proximal end and a rod engaging member distal end, the rod engaging member disposed within the inner passageway and adapted to move from an extended position in which the rod engaging member distal end is disposed outside of the inner passageway to a chambered position in which the rod entire engaging member distal end is disposed within the inner passageway; a movable arm attached to the main body, the movable arm movable between a retracted position on a first side of the main body proximal end and an extended position on a second, opposite side of the main body proximal end; and
   an adjustment mechanism disposed through the proximal opening and operably connected to the rod engaging member proximal end, the adjustment mechanism adapted to cause axial movement of the rod engaging member within the inner passageway upon activation of the adjustment mechanism.

2. The rod insertion tool of claim 1, wherein the inner passageway has a main portion and a distal portion, the distal portion terminating at the distal opening and the main portion extending from the proximal opening to the distal portion; and wherein the distal portion defines a chamber having an inner width that is greater than an inner diameter of the inner passageway in the main portion.

3. The rod insertion tool of claim 2, wherein the main body includes one or more facets that cooperatively define a portion of the chamber.

4. The rod insertion tool of claim 3, wherein the main body includes one or more frustoconical surfaces that cooperatively define a portion of the chamber.

5. The rod insertion tool of claim 1, wherein the rod engaging member distal end defines an engaging structure comprising first and second arms that extend distally from the rod engaging member.

6. The rod insertion tool of claim 5, wherein the first and second arms are disposed substantially opposite each other.

7. The rod insertion tool of claim 6, wherein the first and second arms define a notch disposed between the first and second arms.

8. The rod insertion tool of claim 7, wherein the notch comprises a u-shaped notch.

9. The rod insertion tool of claim 5, further comprising a first inwardly-projecting shoulder disposed on the first arm.

10. The rod insertion tool of claim 9, further comprising a second inwardly-projecting shoulder disposed on the second arm.

11. The rod insertion tool of claim 1, further comprising an internal threaded member disposed on the rod engaging member proximal end, the internal threaded member defining a first thread; and
    wherein the adjustment mechanism defines a second thread that interfaces with the first thread.

12. The rod insertion tool of claim 11, wherein the adjustment mechanism is fixedly secured to the main body such that rotational movement of the second thread results in linear movement of the rod engaging member.

13. The rod insertion tool of claim 11, wherein the internal threaded member is fixedly secured to the rod engaging member proximal end.

14. The rod insertion tool of claim 11, wherein the internal threaded member is integrally formed by the rod engaging member proximal end.

15. The rod insertion tool of claim 11, further comprising a locking mechanism comprising a movable shaft adapted to selectively prevent movement of the rod engaging member.

16. The rod insertion tool of claim 1, further comprising a movable arm attached to the main body, the movable arm movable between a retracted position on a first side of the main body proximal end and an extended position on a second, opposite side of the main body proximal end.

17. The rod insertion tool of claim 16, wherein the main body includes a central longitudinal axis; and
    wherein the movable arm moves from the retracted position to the extended position along a plane that includes the central longitudinal axis.

18. The rod insertion tool of claim 16, wherein the handle defines a channel that receives a portion of the movable arm when the movable arm is in the retracted position.

19. A rod insertion tool, comprising:

a handle;

a main body connected to the handle, the main body having a main body proximal end defining a proximal opening, a main body distal end defining a distal opening, an inner passageway extending between the proximal and distal openings and defining a distal chamber, and one or more frustoconical surfaces that cooperatively define a portion of the chamber;

a rod engaging member having a rod engaging member proximal end and a rod engaging member distal end, the rod engaging member disposed within the inner passageway and adapted to move from an extended position in which the rod engaging member distal end is disposed outside of the inner passageway to a chambered position in which the rod entire engaging member distal end is disposed within the inner passageway;

an adjustment mechanism disposed through the proximal opening and operably connected to the rod engaging member proximal end, the adjustment mechanism adapted to cause axial movement of the rod engaging member within the inner passageway upon activation of the adjustment mechanism; and a movable arm attached to the main body, the movable arm movable between a retracted position on a first side of the main body proximal end and an extended position on a second, opposite side of the main body proximal end.

* * * * *

UNITED STATES PATENT AND TRADEMARK OFFICE
CERTIFICATE OF CORRECTION

PATENT NO. : 9,005,205 B2  
APPLICATION NO. : 13/783728  
DATED : April 14, 2015  
INVENTOR(S) : Craig Black et al.

Page 1 of 1

It is certified that error appears in the above-identified patent and that said Letters Patent is hereby corrected as shown below:

In the Claims

Col. 12, Claim 1, line 14 reads --in which the rod entire engaging member--.

Col. 12, Claim 1, line 14 should read --in which the entire rod engaging member--.

Col. 14, Claim 19, line 16 reads --in which the rod entire engaging member--.

Col. 14, Claim 19, line 16 should read --in which the entire rod engaging member--.

Signed and Sealed this  
Fifteenth Day of September, 2015

Michelle K. Lee  
*Director of the United States Patent and Trademark Office*